(12) United States Patent
Song

(10) Patent No.: US 7,575,887 B2
(45) Date of Patent: Aug. 18, 2009

(54) DETECTION OF PROTEASES SECRETED FROM PATHOGENIC MICROORGANISMS

(75) Inventor: Xuedong Song, Roswell, GA (US)

(73) Assignee: Kimberly-Clark, Worldwide, Inc.

( * ) Notice: Subject to any disclaimer, the term of this patent is extended or adjusted under 35 U.S.C. 154(b) by 297 days.

(21) Appl. No.: 11/364,810

(22) Filed: Feb. 28, 2006

(65) Prior Publication Data

US 2007/0048816 A1 Mar. 1, 2007

Related U.S. Application Data

(63) Continuation-in-part of application No. 11/217,097, filed on Aug. 31, 2005.

(51) Int. Cl.
*C12Q 1/37* (2006.01)
(52) U.S. Cl. ....................................................... 435/23
(58) Field of Classification Search ........................ None
See application file for complete search history.

(56) References Cited

U.S. PATENT DOCUMENTS

| | | |
|---|---|---|
| 3,700,623 A | 10/1972 | Keim |
| 3,772,076 A | 11/1973 | Keim |
| 4,140,580 A | 2/1979 | Gibson et al. |
| 4,275,149 A | 6/1981 | Litman et al. |
| 4,537,657 A | 8/1985 | Keim |
| 4,614,723 A | 9/1986 | Schmidt et al. |
| 4,637,979 A | 1/1987 | Skjold et al. |
| 4,748,116 A | 5/1988 | Simonsson et al. |
| 4,806,423 A | 2/1989 | Hugl et al. |
| 4,814,271 A | 3/1989 | Hugl et al. |
| 4,859,581 A | 8/1989 | Nicolson et al. |
| 4,874,695 A | 10/1989 | Pincus |
| 5,075,077 A | 12/1991 | Durley, III et al. |
| 5,124,254 A | 6/1992 | Hewlins et al. |
| 5,252,459 A | 10/1993 | Tarcha et al. |
| 5,292,652 A | 3/1994 | Dovey et al. |
| 5,328,831 A | 7/1994 | Stewart et al. |
| 5,449,612 A | 9/1995 | Lepargneur et al. |
| 5,464,739 A | 11/1995 | Johnson et al. |
| 5,464,741 A | 11/1995 | Hendrix |
| 5,518,883 A | 5/1996 | Soini |
| 5,571,684 A | 11/1996 | Lawrence et al. |
| 5,573,909 A | 11/1996 | Singer et al. |
| 5,585,273 A | 12/1996 | Lawrence et al. |
| 5,585,279 A | 12/1996 | Davidson |
| 5,591,581 A | 1/1997 | Massey et al. |
| 5,637,509 A | 6/1997 | Hemmilä et al. |
| 5,670,381 A | 9/1997 | Jou et al. |
| 5,731,147 A | 3/1998 | Bard et al. |
| 5,786,137 A | 7/1998 | Diamond et al. |
| 5,922,537 A | 7/1999 | Ewart et al. |
| 6,004,530 A | 12/1999 | Sagner et al. |
| 6,022,698 A | 2/2000 | Chen et al. |
| 6,030,840 A | 2/2000 | Mullinax et al. |
| 6,197,537 B1 | 3/2001 | Rao et al. |
| 6,235,464 B1 | 5/2001 | Henderson et al. |
| 6,242,268 B1 | 6/2001 | Weider et al. |
| 6,243,980 B1 | 6/2001 | Bronstein et al. |
| 6,261,779 B1 | 7/2001 | Barbera-Guillem et al. |
| 6,287,798 B1 | 9/2001 | James et al. |
| 6,306,642 B1 | 10/2001 | Nelson |
| 6,348,319 B1 | 2/2002 | Braach-Maksvytis et al. |
| 6,362,011 B1 | 3/2002 | Massey et al. |
| 6,402,918 B1 | 6/2002 | Schlenoff et al. |
| 6,444,423 B1 | 9/2002 | Meade et al. |
| 6,451,619 B1 | 9/2002 | Catt et al. |
| 6,468,741 B1 | 10/2002 | Massey et al. |
| 6,472,141 B2 | 10/2002 | Nikiforov |
| 6,485,926 B2 | 11/2002 | Nemori et al. |
| 6,528,321 B1 | 3/2003 | Fitzgerald et al. |
| 6,582,930 B1 | 6/2003 | Ponomarev et al. |

(Continued)

FOREIGN PATENT DOCUMENTS

EP 0698600 A1 * 2/1996

(Continued)

OTHER PUBLICATIONS

Carricajo et al. "Comparative eveluation of five chromogenic media for detection, enumeration and identification of urinary tract pathogens" Eur J Clin Microbiol Infect Dis 1999, 18:796-803.*

(Continued)

*Primary Examiner*—Jon P Weber
*Assistant Examiner*—Bin Shen
(74) *Attorney, Agent, or Firm*—Dority & Manning, P.A.

(57) ABSTRACT

A diagnostic test kit for detecting the presence or absence of a protease (e.g., aminopeptidase) within a test sample is provided. The test kit comprises a substrate that is capable of being cleaved in the presence of the protease to release a compound. The kit also comprises a lateral flow device that comprises a chromatographic medium. The chromatographic medium defines a detection zone within which is contained a first reagent (e.g., diazonium ion) that is capable of reacting with the compound to form a second reagent (e.g., aromatic azo compound). The second reagent exhibits a color that is different than the color of the first reagent. The lateral flow device also includes an absorbent material located adjacent to the chromatographic medium, the absorbent material receiving the test sample after flowing through the chromatographic medium.

12 Claims, 2 Drawing Sheets

U.S. PATENT DOCUMENTS

| | | |
|---|---|---|
| 6,585,939 B1 | 7/2003 | Dapprich |
| 6,613,583 B1 | 9/2003 | Richter et al. |
| 6,623,955 B2 | 9/2003 | Matner et al. |
| 7,041,469 B2 | 5/2006 | Lawrence et al. |
| 7,094,528 B2 | 8/2006 | Song et al. |
| 2001/0046668 A1 | 11/2001 | Levine et al. |
| 2002/0127623 A1 | 9/2002 | Minshull et al. |
| 2003/0073147 A1 | 4/2003 | Alderete et al. |
| 2003/0108978 A1 | 6/2003 | Ciambrone et al. |
| 2003/0119073 A1 | 6/2003 | Quirk et al. |
| 2003/0119202 A1 | 6/2003 | Kaylor et al. |
| 2003/0119204 A1 | 6/2003 | Wei et al. |
| 2003/0124739 A1 | 7/2003 | Song et al. |
| 2004/0002110 A1 | 1/2004 | Boga et al. |
| 2004/0029205 A1 | 2/2004 | Small, Jr. et al. |
| 2004/0043502 A1 | 3/2004 | Song et al. |
| 2004/0043507 A1 | 3/2004 | Song et al. |
| 2004/0043511 A1 | 3/2004 | Song et al. |
| 2004/0043512 A1 | 3/2004 | Song et al. |
| 2004/0081971 A1 | 4/2004 | Yue et al. |
| 2004/0106190 A1 | 6/2004 | Yang et al. |
| 2004/0121334 A1 | 6/2004 | Wei et al. |
| 2004/0121480 A1 | 6/2004 | Wei |
| 2005/0112703 A1 | 5/2005 | Song |
| 2005/0112780 A1 | 5/2005 | Song |
| 2005/0124072 A1 | 6/2005 | Boga |
| 2005/0136529 A1 | 6/2005 | Yang et al. |
| 2005/0136550 A1 | 6/2005 | Yang et al. |
| 2005/0191704 A1 | 9/2005 | Boga et al. |
| 2005/0220712 A1 | 10/2005 | Wright et al. |
| 2005/0233368 A1 | 10/2005 | Beall et al. |
| 2005/0243321 A1 | 11/2005 | Cohen et al. |
| 2005/0244643 A1 | 11/2005 | Song et al. |
| 2006/0003336 A1 | 1/2006 | Song et al. |
| 2006/0003394 A1 | 1/2006 | Song |
| 2006/0019265 A1 | 1/2006 | Song et al. |
| 2006/0057661 A1 | 3/2006 | Song et al. |
| 2006/0127459 A1 | 6/2006 | Huang et al. |
| 2007/0048182 A1 | 3/2007 | Song et al. |
| 2007/0048807 A1 | 3/2007 | Song |
| 2007/0048815 A1 | 3/2007 | Song |
| 2007/0048816 A1 | 3/2007 | Song |
| 2007/0134747 A1 | 6/2007 | DiGiammarino et al. |

FOREIGN PATENT DOCUMENTS

| | | |
|---|---|---|
| EP | 0864864 A1 | 9/1998 |
| WO | WO 9714028 | 4/1997 |
| WO | WO 03023051 A2 | 3/2003 |
| WO | WO 03023051 A3 | 3/2003 |
| WO | WO 2005066359 A1 | 7/2005 |
| WO | WO 2005098020 A1 | 10/2005 |
| WO | WO 2006079826 A1 | 8/2006 |
| WO | WO 2007096637 A1 | 8/2007 |
| WO | WO 2007128980 A1 | 11/2007 |

OTHER PUBLICATIONS

Lammers et al. "Comparison of test characteristics of urine dipstick and urinalysis at various test cutoff points" Annals of Emergency Medicine, 2001, 38(5):505-512.*

Naglik et al. "*Candida albicans* proteinases and host/pathogen interactions" Cellular Microbiology, 2004, 6(10):915-926.*

L.J. Jones et al.—Quenched BODIPY Dye-Labeled Casein Substrates for the Assay of Protease Activity by Direct Fluorescence Measurement—Published, *Analytical Biochemistry 251*, 144-152 (1997) Article No. AB972259.

J.M. Steiner et al.—Development and analytic validationof an enzyme-linked immunosorbent assay for the measurement of canine pancreatic lipase immunoreactivity in serum—Published, *The Canadian Journal of Veterinary Research 2003*; 67:175-182.

H. Rahimi et al.—Monoclonal antibodies against *Candida* rugosa lipase—Published, *Journal of Molecular Catalysts B: Enzymatic 28* (2004) 71-74.

D.A. Schofield et al.—Differential *Candida albicans* lipase gene expression during alimentary tract colonization and infection—Published, *FEMS Microbiology Letters 244* (2005) 359-365.

F. Stehr et al.,—Expression analysis of the *Candida albicans* lipase gene family during experimental infections and in patient samples—Published, *FEMS Yeast Research 4* (2004) 401-408.

Englert et al.—Layered Expression Scanning: Rapid Molecular Profiling of Tumor Samples—Published, *Cancer Research 60*, 1526-1530, Mar. 15, 2000.

A.W. Kusterbeck et al.- Use of the USDT flow immunosensor for quantitation of benzoylecgonine in urine—Published, *Elsevier Science Limited, Biosensors & Bioelectronics* vol. 11 No. 8 pp. 725-734, 1996.

D.J. Pritchard et al.—Simultaneous determination of follicle stimulating hormone and luteinising hormone using multianalyte immunosensor—Published, *Elsevier, Analytica Chimica Acta 310* (1995) 251-256.

L.M. Golub et al.—A matrix metalloproteinase inhibitor reduces bone-type collagen degradation fragments and specific collagenases in gingival crevicular fluid during adult periodontitis—Published, *Inflamm. res.* 46 (1997) 310-319.

K. Brew et al.—Tissue inhibitors of metalloproteinases: evolution, structure and function—Published, *Elsevier—Biochimica et Biophysica Acta 1477* (2000) 267-283.

B. Stratmann et al.—MMP-TIMP interaction depends on residue 2 in TIMP-4—Published, *FEBS Letters 507* (2001) 285-287.

Yuan et al.—*A New Tetradentate β-Diketonate-Europium Chelate That Can Be Covalently Bound to Proteins for Time-Resolved Fluoroimmunoassay*, Analytical Chemistry, vol. 70, No. 3, Feb. 1, 1998, pp. 596-601.

Lövgren et al—*One-step all-in-one dry reagent immunoassays with fluorescent europium chelate label and time-resolved fluorometry,.* Clinical Chemistry, vol. 42, No. 8, 1996, pp. 1196-1201.

Article—*Identification of Different Candida Species Isolated in Various Hospitals in Ankara by Fungichrom Test Kit and Their Differentiation by SED-PAGE*, Osmanağaoğlu et al., Turk. J. Med. Sci., vol. 30, 2000, pp. 355-358.

Article—*Transcriptional Response of Candida ablicans upon Internalization by Macrophages*, Lorenz et al., *Eukaryotic* Cell, vol. 3. No. 5, Oct. 2004, pp. 1076-1087.

Song et al., U.S. Appl. No. 11/119,262, filed Apr. 29, 2005, Assay Devices Having Detection Capabilities within the Hook Effect Region.

Song et al., U.S. Appl. No. 11/094,498, filed Mar. 30, 2005, Diagnostic Test Kits Employing an Internal Calibration System.

Xuedong Song, U.S. Appl. No. 11/217,112, filed Aug. 31, 2005, Diagnostic Test Kits with Improved Detection Accuracy.

Xuedong Song, U.S. Appl. No. 11/217,097, filed Aug. 31, 2005, Enzyme Detection Technique.

Song et al., U.S. Appl. No. 11/217,099, filed Aug. 31, 2005, Nitrite Detection Technique.

Takeuchi et al., U.S. Appl. No. 11/301,631, filed Dec. 13, 2005, Metering Technique for Lateral Flow Assay Devices.

Xuedong Song., U.S. Appl. No. 11/399,687, filed Apr. 6, 2006, Enzymatic Detection Techniques.

Search Report and Written Opinion for PCT/US2006/030107, Apr. 18, 2007.

* cited by examiner

DETECTION OF PROTEASES SECRETED FROM PATHOGENIC MICROORGANISMS

RELATED APPLICATIONS

The present application is a continuation-in-part application of U.S. patent application Ser. No. 11/217,097, filed on Aug. 31, 2005.

BACKGROUND OF THE INVENTION

The most common vaginal infections include vulvovaginal candidiasis, bacterial vaginosis, and trichomoneasis. While symptomatically these infections may appear quite similar, the particular pathogenic microorganism underlying each may vary widely. For instance, candidiases are caused by pathogenic strains of yeast belonging to the genera *Candida* or related strains belonging mainly to the genera of *Torulopsis*. Trichomoneasis, on the other hand, is caused by the parasite *Trichomonas vaginalis*, and the underlying cause of bacterial vaginosis often cannot be attributed to one specific etiologic agent. Moreover, often these pathogens are common and/or benign, and only under opportune conditions will they become pathogenic. For instance, the species *Candida albicans* is the most common fungal pathogen of humans and one of the most common microorganisms isolated from blood cultures. Depending upon underlying host health and condition, benign *C. albicans* may become virulent and cause infections ranging from vulvovaginal candidiasis to life-threatening disseminated candidiasis that is able to infect virtually every organ of the host.

While the pathogens causing these types of vaginal infections may vary widely, they often share common traits. For instance, many of these pathogens express common enzymes including a variety of proteases, i.e., peptidases and proteinases. Moreover, expression of particular proteases is often upregulated by the pathogenic form of the causative agent (see, e.g., Lorenz, et al., *Eukaryotic Cell*, 3, pp. 1076-1087 (2004)).

In many cases, self-treatment of these diseases is possible, but this requires an accurate diagnosis early in the disease process. What is needed in the art are accurate yet relatively simple methods and devices for recognizing the presence of pathogens that cause such diseases. For instance, a device that could provide a self-diagnosis route for the presence of opportunistic *C. albicans* could be of great benefit to consumers.

SUMMARY OF THE INVENTION

In accordance with one embodiment of the present invention, disclosed is a diagnostic test kit for detecting within a test sample the presence or absence of a protease secreted by a pathogenic organism. The test kit comprises a substrate that is capable of being cleaved in the presence of the protease to release a chromogenic product. In particular, the substrate comprises a peptide bond. The kit also includes a lateral flow device that comprises a chromatographic medium. The chromatographic medium defines a detection zone within which is contained a first reagent (e.g., diazonium ion) that is capable of reacting with the chromogenic product to form a second reagent (e.g., aromatic azo compound). The second reagent exhibits a color that is different than the color of the first reagent. The lateral flow device also includes an absorbent material that receives the test sample after flowing through the chromatographic medium.

In another embodiment, the present invention is directed to a method for detecting a protease in a test sample. For example, the method may include contacting a lateral flow device of the invention, for example, a lateral flow device such as that found in the test kits described herein, with the test sample and generating a detectable signal at the detection zone that corresponds to the presence or absence of the protease.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figure in which.

Figure 1:
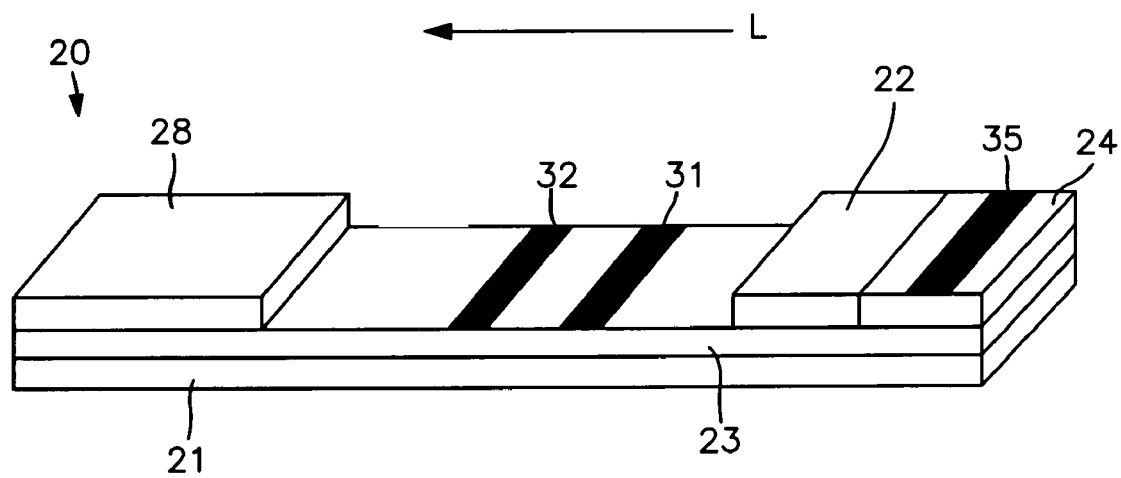
FIG. 1 is a perspective view of one embodiment of a lateral flow device that may be used in the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "test sample" generally refers to any material suspected of containing a protease. The test sample may be derived from any biological source, such as a physiological fluid, including, blood, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen, and so forth. Besides physiological fluids, other liquid samples may be used such as water, food products, and so forth, for the performance of environmental or food production assays. In addition, a solid material suspected of containing the protease may be used as the test sample. The test sample may be used directly as obtained from the biological source or following a pretreatment to modify the character of the sample. For example, such pretreatment may include preparing plasma from blood, diluting viscous fluids, and so forth. Methods of pretreatment may also involve filtration, precipitation, dilution, distillation, mixing, concentration, inactivation of interfering components, the addition of reagents, lysing, etc. Moreover, it may also be beneficial to modify a solid test sample to form a liquid medium or to release the protease.

As used herein, the term "protein" refers to any molecular chain of amino acids that is capable of interacting structurally, enzymatically or otherwise with other proteins, polypeptides or any other organic or inorganic molecule.

As used herein, the term "polypeptide" refers to a molecular chain of amino acids and does not refer to a specific length of the product. Thus, peptides, oligopeptides and proteins are included within the definition of polypeptide. This term is also intended to include polypeptides that have been subjected to post-expression modifications such as, for example, glycosylations, acetylations, phosphorylations, and so forth.

As used herein, the term "protease" refers to any of various enzymes that catalyze the hydrolytic breakdown of proteins into smaller segments, including polypeptides and/or amino acids. Accordingly, included in the definition are proteinases and peptidases.

As used herein, the term "proteinase" refers to a protease that catalyzes the hydrolytic breakdown of proteins by splitting them into smaller peptide fractions, i.e., polypeptides or amino acids.

As used herein, the term "peptidase" refers to a protease that catalyzes the hydrolytic breakdown of peptides via cleavage of an individual amino acid from the peptide chain.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a device for detecting the presence of a protease in a test sample. The protease may be expressed and/or upregulated by one or more pathogens responsible for common vaginal infections, such as bacterial vaginosis, trichomoneasis, and vulvovaginal candidiasis. For example, the expression of the detected protease may be upregulated by the pathogenic form of a *Candida* species (e.g., *C. albicans*), which may aid in the diagnosis of a yeast infection or disseminated candidiasis. Proteases (e.g., proline iminopeptidase) may also be detected in accordance with the present invention that are expressed and/or upregulated by bacterial pathogens found in vaginal fluids.

The technique of the present invention employs a variety of reagents for detecting the protease. One such reagent is a substrate that includes a peptide bond. The substrate is chemically acted upon or "cleaved" by the protease of interest to release a chromogenic product. The chromogenic product thus released is capable of conversion to a secondary product that is then recognizable. For example, the released chromogenic product may react with a first reagent to form a second reagent that has a discernable color. Examples of such second reagents and their reaction products are further described below.

In one embodiment, the substrates of the present invention can include one or more aromatic rings, in addition to the peptide bond. According to this embodiment, the aromatic groups may be substituted or unsubstituted. Specific examples of possible aromatic groups may include, for instance, substituted or unsubstituted 4-aminoantipyrine, tetramethylbenzine, 2,2'-azino-bis(3-ethyl-benzthiazoline-6-sulfonic) acid, and so forth.

In one particular embodiment, the invention is directed to the detection of secreted aminoproteases. When detecting an aminoprotease, for example, the substrate may include a peptide or polypeptide that is catalytically hydrolyzed in the presence of the aminoprotease to yield an aromatic compound. The aromatic substrates may include, for instance, β-naphthylamide substrates having the following general formula:

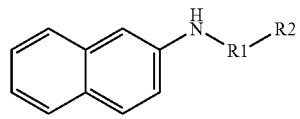

wherein,

R1 may be a monoamino acid residue or a peptide residue, and

R2 may be a hydrogen atom or any other suitable group blocking the N-terminal end of the substrate. For example, R2 may be substituted or unsubstituted, and may be an alkyl group, an alkyoxy group, a hydroxyalkyl group, an alkylene group, a fatty acid group, and so forth.

The amino acid or peptide derivatized substrates are hydrolyzed by the protease. For instance, a β-naphthylamide substrate may be hydrolyzed by an aminoprotease to form a β-naphthylamine, which has the following structure:

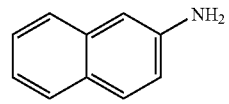

The monoamino acid or peptide residue of the substrate may be selected as one that is susceptible to cleavage by an aminoprotease of interest. The reagents utilized in the disclosed devices may thus be selected to specifically target an protease of interest. For example, certain aminopeptidases, e.g., homologs of aminopeptidase I (ScLAP4) are upregulated upon the transition of *C. albicans* from the benign commensal form to the pathogenic hyphal form (see, e.g., Lorenz, et al., *Eukaryotic Cell*, 3, pp. 1076-1087 (2004). Accordingly, a substrate may be utilized including a residue susceptible to cleavage by one of these upregulated aminopeptidases, in order to more accurately diagnose the presence of hyphal *C. albicans* in a host.

Other suitable substrates for proteases include, for instance, proteins or glycoproteins, peptides, and so forth. For instance, some suitable substrates for peptidases and/or proteinases may include peptides, proteins, and/or glycoproteins such as casein (e.g., β-casein, azocasein, etc.), albumin (e.g., bovine serum albumin), hemoglobin, myoglobin, keratin, gelatin, insulin, proteoglycan, fibronectin, laminin, collagen, elastin, and so forth. Still other suitable substrates are described in U.S. Pat. Nos. 5,449,612 to Lepargneur, et al.; 4,874,695 to Pincus; 6,022,698 to Chen, et al.; and 5,571,684 to Lawrence, et al., which are incorporated herein in their entirety by reference thereto for all purposes.

If desired, the rate of the protease-catalyzed reaction may be selectively controlled using techniques known in the art, such as controlling the temperature, pH, substrate concentration, the presence of accelerators, the presence of inhibitors (competitive (binds to protease), uncompetitive (binds to protease-substrate complex), or noncompetitive (binds to protease and/or protease-substrate complex)), and so forth. These factors may be selectively controlled as desired to increase or decrease the reaction time. For example, an accelerator may be employed to enhance protease activity. Suitable accelerators for hydrolytic proteases may include, for instance, pyridine, imidazole and their derivatives, metal complexes, and alcohols. The pH may also be selectively controlled to enhance protease activity and to inhibit unwanted side reactions. For instance, many substrates are unstable in highly basic or highly acidic conditions due to their tendency to hydrolyze. Thus, the pH is typically maintained at a relatively neutral level, such as from about 6 to about 9, and in some embodiments, about 7. Some biologically compatible buffers that may be used to maintain the desired pH include borate buffers, phosphate-buffered saline (PBS), 2-(N-morpholino) ethane sulfonic acid ("MES"), trishydroxymethylaminomethane ("Tris"), citrate buffers, and so forth.

Regardless of the manner in which the reaction is conducted, through cleavage of the substrate a chromogenic product is released that is capable of inducing a color change in the presence of certain reagents. In one particular embodiment, the released chromogenic product may be an aromatic compound that is a nucleophile in that it contains a group that is electron rich (e.g., amine) and that may form bonds with electron deficient groups. For example, β-naphthylamides may be hydrolyzed by a protease to form β-naphthylamine. β-naphthylamine contains an electron-rich, aromatic ring system that is capable of undergoing electrophilic attack by a diazonium ion having the generic formula:

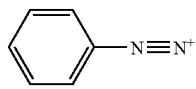

The diazonium ion may be zwitterionic in that the counterion of the diazonium moiety is covalently bound to the ring system. The ring system of the diazonium ion may be substituted or unsubstituted. The ion may be provided by a variety of suitable diazonium salts, such as diazonium chlorides, diazonium acid sulphates, diazonium alkyl sulphates, diazonium fluoborates, diazonium benzenesulphonates, diazonium acid 1,5-naphthalenedisulphonates, and so forth. Specific examples of diazonium salts are 1-diazo-2-naphthol-4-sulfonate; 1-diazophenyl-3-carbonate; 4-diazo-3-hydroxy-1-naphthylsulfonate (DNSA); 4-diazo-3-hydroxy-7-nitro-1-naphthylsulfonate (NDNSA); 4-diazo-3-hydroxy-1,7-naphthyldisulfonate; 2-methoxy-4-(N-morpholinyl) benzene diazonium chloride; 4-diazo-3-hydroxy-7-bromo-1-naphthylsulfonate; and 4-diazo-3-hydroxy-7-[1,oxopropyl]-1-naphthylsulfonate. One particularly desired diazonium salt is 5-chloro-2-methoxybenzenediazonium chloride, which has a yellow color and is classified under the name "Diazo Red RC" or "Fast Red RC." More specifically, "Fast Red RC" has the following structure:

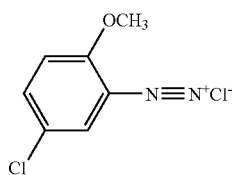

Other suitable diazonium salts are classified by the common names "Fast Red B" and "Fast Blue B." Still other suitable diazonium salts may be described in U.S. Pat. Nos. 4,637,979 to Skjold, et al.; 4,806,423 to Hugh, et al.; and 4,814,271 to Hugl, et al., which are incorporated herein in their entirety by reference thereto for all purposes.

In some cases, it may be desirable to select the chromogenic product based on its ability to be readily immobilized onto a solid substrate. In this regard, certain macromolecular reagents (e.g., polymers, oligomers, dendrimers, particles, etc.) may be particularly useful in the present invention. Generally speaking, such macromolecular reagents contain at least two functionalities, i.e., a reactive moiety (e.g., diazonium ion) and a macromolecular moiety, which are covalently or noncovalently joined. The macromolecular moiety may include, for instance, a polymeric moiety, such as a linear or branched, homopolymer or copolymer. The polymeric moieties may be natural, synthetic, or combinations thereof. Examples of natural polymeric moieties include, for instance, peptides, proteins, DNA/RNA and polysaccharides (e.g., glucose-based polymers). Examples of synthetic polymeric moieties include, instance, polyacrylic acid and polyvinyl alcohols.

As indicated, the macromolecular moiety may also be a particle (sometimes referred to as a "bead" or "microbead"). Naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex microparticles that are labeled with a fluorescent or colored dye are utilized. Although any synthetic particle may be used in the present invention, the particles are typically formed from polystyrene, butadiene styrenes, styrene-acrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 1,000 microns, in some embodiments, from about 0.1 nanometers to about 100 microns, and in some embodiments, from about 1 nanometer to about 10 microns.

The particle may generally be joined to a reactive moiety using any of a variety of well-known techniques. For instance, covalent attachment of a particle to a substrate may be accomplished using carboxylic, amino, aldehyde, bromoacetyl, iodoacetyl, thiol, epoxy or other reactive functional groups, as well as residual free radicals and radical cations, through which a coupling reaction may be accomplished. A surface functional group may also be incorporated as a functionalized co-monomer because the surface of the particle may contain a relatively high surface concentration of polar groups. In certain cases, the particle may be capable of direct covalent bonding to a substrate without the need for further modification. It should also be understood that, besides covalent bonding, other attachment techniques, such as physical adsorption, may also be utilized in the present invention.

As indicated above, the nucleophilic aromatic compounds released by the hydrolysis of the substrate are capable of undergoing electrophilic attack by a reagent (e.g., diazonium ion). This reaction is often referred to as "coupling" and results in the formation of another reagent having a different color. For example, diazonium ions may react with aromatic compounds to form an aromatic azo compound having the generic formula, R—N=N—R', wherein "R" and "R'" are aryl groups. Without intending to be limited by theory, it is believed that this reaction induces either a shift of the absorption maxima towards the red end of the spectrum ("bathochromic shift") or towards the blue end of the spectrum ("hypsochromic shift"). The type of absorption shift depends on the nature of the resulting azo molecule and whether it functions as an electron acceptor (oxidizing agent), in which a hypsochromic shift results, or whether it functions as an electron donor (reducing agent), in which a bathochromic shift results. Regardless, the absorption shift provides a color difference that is detectable, either visually or through instrumentation, to indicate the presence of protease within the test sample. For example, prior to contact with an infected test sample, the diazonium ion may be colorless or it may possess a certain color. However, after contacting the test sample and reacting with an aromatic compound released by hydrolysis of the substrate, an aromatic azo compound will form that exhibits a color that is different than the initial color of the diazonium ion. Exemplary aromatic azo compounds that may be formed include dimethyldiazene, diphenydiazene, 1-naphthyl-2-naphthyl diazene, 3-chlorophenyl-4-chlorophenyl diazene, methylvinyl diazene, and 2-naphthylphenyl diazene. In one particular embodiment, for instance, "Fast Red RC" (yellow), a diazonium ion, may react with β-naphylamine to form an aromatic azo compound that is red and has the following general structure (may be substituted or unsubstituted):

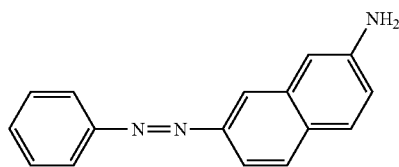

It should be understood that the chromogenic products released due to the hydrolysis of the substrate by the protease are not limited to aromatics. In particular, the released chromogenic products may be any material that may be discernable following reaction with a reagent. For example, in one embodiment, the chromogenic product may include one or more amino acids. One embodiment of a chromogenic system that may be used when the chromogenic product includes an amino acid is described in U.S. Pat. No. 5,571,684 to Lawrence, et al., previously incorporated by reference. Such a chromogenic system may comprise an amino acid oxidase, a chromogen selected from the group consisting of guaiac, 2,2'-azino-bis(3-ethyl-benzthiazoline-6-sulfonic acid), tetramethylbenzidine, phenol, 4-aminoantipyrine and 4,5-dihydroxynaphthalene, a redox catalyst selected from the group consisting of peroxidases, iron protoporphyrin and metal ions, and oxygen. Schematically, this system may be illustrated as follows:

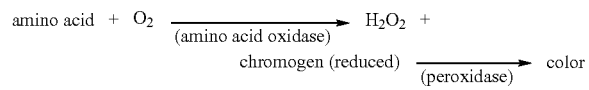

Of course, the most appropriate reagent for any given released chromogenic product will depend at least upon the substrate specificity of the protease, the actual chromogenic product released, and the reaction conditions needed for a given test. The selection in any given case will be readily apparent to those skilled in the art.

As a result of the color change following cleavage of the substrate by the protease, the presence of the protease in a test sample may be readily detected. The extent of the color change may be selectively controlled in accordance with the present invention to limit "false positives." More specifically, a small and perhaps normal amount of protease within a test sample may hydrolyze a substrate to release a nucleophilic aromatic compound.

In some cases, however, the released aromatic compound may undergo an oxidation reaction if left in air or other oxidizing environment for too great a period of time. The resulting color of the oxidized compound may indicate a "false positive" or at the very least, adversely affect the ability to semi-quantitatively or quantitatively determine the presence of the protease. In other cases, the reaction is advantageously stopped following a desired reaction time so as to avoid generation of a false positive. Thus, the present inventor has discovered a technique for reducing the problem of such "false positives." Beneficially, the technique requires no additional reagents, for instance to stop the reaction. Instead of simply measuring the results after a certain period of time, the desired reaction time may be achieved by selectively controlling the medium in which the reaction occurs. That is, the reaction medium is chromatographic in nature such that the protease and substrate are allowed to flow in a consistent and controllable manner. While flowing through the medium, the protease and substrate react to release chromogenic product that subsequently couples with a reagent such as a diazonium ion to form a detectable reagent, e.g., an aromatic azo compound. The aromatic azo compound is immobilized within a discrete detection region for analysis. Due to the nature of the controlled fluid flow, any unreacted substrate travels to the end of the reaction medium so that it is unable to adversely interfere with observance of the aromatic azo compound in the detection region. At the same time, the aromatic compounds that are released from the end of the reaction medium will not react with the reagents in the detection zone to generate potential false positives.

Various embodiments for accomplishing the detection of the protease using fluid flow control techniques will now be described in more detail. Referring to FIG. 1, for instance, one embodiment of a lateral flow device 20 that may be formed according to the present invention will now be described in more detail. As shown, the device 20 contains a chromatographic medium 23 optionally supported by a rigid support material 21. In general, the chromatographic medium 23 may be made from any of a variety of materials through which the test sample is capable of passing. For example, the chromatographic medium 23 may be a porous membrane formed from synthetic or naturally occurring materials, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the chromatographic medium 23 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The size and shape of the chromatographic medium 23 may generally vary as is readily recognized by those skilled in the art. For instance, a porous membrane strip may have a length of from about 10 to about 100 millimeters, in some embodiments from about 20 to about 80 millimeters, and in some embodiments, from about 40 to about 60 millimeters. The width of the membrane strip may also range from about 0.5 to about 20 millimeters, in some embodiments from about 1 to about 15 millimeters, and in some embodiments, from about 2 to about 10 millimeters. Likewise, the thickness of the membrane strip is generally small enough to allow transmission-based detection. For example, the membrane strip may have a thickness less than about 500 micrometers, in some embodiments less than about 250 micrometers, and in some embodiments, less than about 150 micrometers.

As stated above, the support 21 carries the chromatographic medium 23. For example, the support 21 may be positioned directly adjacent to the chromatographic medium 23 as shown in FIG. 1, or one or more intervening layers may be positioned between the chromatographic medium 23 and the support 21. Regardless, the support 21 may generally be formed from any material able to carry the chromatographic medium 23. The support 21 may be formed from a material that is transmissive to light, such as transparent or optically diffuse (e.g., transluscent) materials. Also, it is generally desired that the support 21 is liquid-impermeable so that fluid flowing through the medium 23 does not leak through the support 21. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. To provide a sufficient structural backing for the chromatographic medium 23, the support 21 is generally selected to have a certain minimum thickness. Likewise, the thickness of the support 21 is typically not so large as to adversely affect its optical properties. Thus, for example, the support 21 may have a thickness that ranges from about 100 to about 5,000 micrometers, in some embodiments from about 150 to about 2,000 micrometers, and in some embodiments, from about 250 to about 1,000 micrometers. For instance, one suitable membrane strip having a thickness of about 125 micrometers may be obtained from Millipore Corp. of Bedford, Mass. under the name "SHF180UB25."

As is well known in the art, the chromatographic medium 23 may be cast onto the support 21, wherein the resulting laminate may be die-cut to the desired size and shape. Alternatively, the chromatographic medium 23 may simply be laminated to the support 21 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate device structures are described in U.S. Pat. No. 5,075,077 to Durley, III, et al., which is incorporated herein in its entirety by reference thereto for all purposes.

The device 20 also contains an absorbent material 28 that is positioned adjacent to the medium 23. The absorbent material 28 assists in promoting capillary action and fluid flow through the medium 23. In addition, the absorbent material 28 receives fluid that has migrated through the entire chromatographic medium 23 and thus draws any unreacted components away from the detection region to help reduce the likelihood of "false positives." Some suitable absorbent materials that may be used in the present invention include, but are not limited to, nitrocellulose, cellulosic materials, porous polyethylene pads, glass fiber filter paper, and so forth. The absorbent material may be wet or dry prior to being incorporated into the device. Pre-wetting may facilitate capillary flow for some fluids, but is not typically required. Also, as is well known in the art, the absorbent material may be treated with a surfactant to assist the wicking process.

To initiate the detection of a protease within the test sample, a user may directly apply the test sample to a portion of the chromatographic medium 23 through which it may then travel in the direction illustrated by arrow "L" in FIG. 1. Alternatively, the test sample may first be applied to a sample application zone 24 that is in fluid communication with the chromatographic medium 23. The sample application zone 24 may be formed on the medium 23. Alternatively, as shown in FIG. 1, the sample application zone 24 may be formed by a separate material, such as a pad. Some suitable materials that may be used to form such sample pads include, but are not limited to, nitrocellulose, cellulose, porous polyethylene pads, and glass fiber filter paper. If desired, the sample application zone 24 may also contain one or more pretreatment reagents, either diffusively or non-diffusively attached thereto. In the illustrated embodiment, the test sample travels from the sample application zone 24 to a reagent zone 22 that is in communication with the sample application zone 24. As described above, the reagent zone 22 may be formed on the medium 23. Alternatively, as shown in FIG. 1, the reagent zone 22 is formed from a separate material or pad. Such a reagent pad may be formed from any material through which the test sample is capable of passing, such as glass fibers.

To facilitate detection of the targeted proteases in the manner described above, a substrate is employed. In some embodiments, the substrate may be mixed with the test sample prior to application to the device 20. Alternatively, the substrate may be diffusively immobilized on the device 20 prior to application of the test sample. Such pre-application provides a variety of benefits, including the elimination of the need for a subsequent user to handle and mix the reagents with the test sample or a diluent. This is particularly useful in point-of-care applications when the user is not generally a trained lab technician or medical professional. The substrate may be disposed downstream from the sample application zone 24. In this manner, the test sample is capable of mixing with the substrate upon application. Alternatively, the substrate may be positioned upstream from the sample application zone 24. For instance, a diluent may be employed to induce mixing between the substrate and test sample.

If desired, the pH may be maintained at a relatively neutral level to facilitate the desired protease-catalyzed reaction, such as described above. To accomplish the desired pH level, a buffer may be mixed with the substrate prior to application to the device 20, mixed with the test sample, or both. Alternatively, the buffer may be separately applied to the lateral flow device 20 so that it is capable of mixing with the reagents upon application to the test sample.

Referring again to FIG. 1, the lateral flow device 20 includes a detection zone 31 within which is immobilized a second reagent, such as a diazonium ion described above. The diazonium ion may be applied directly to the medium 23 or first formed into a solution prior to application. Various solvents may be utilized to form the solution, such as, but not limited to, acetonitrile, dimethylsulfoxide (DMSO), ethyl alcohol, dimethylformamide (DMF), and other polar organic solvents. For instance, the amount of a diazonium salt in the solution may range from about 0.001 to about 100 milligrams per milliliter of solvent, and in some embodiments, from about 0.1 to about 10 milligrams per milliliter of solvent. In one particular embodiment, the detection zone 31 is defined by the chromatographic medium 23 and formed by coating a solution thereon using well-known techniques and then dried. The diazonium ion concentration may be selectively controlled to provide the desired level of detection sensitivity.

Typically, it is desired that the diazonium ion be applied in a manner so that it does not substantially diffuse through the matrix of the chromatographic medium 23 (i.e., non-diffusively immobilized). This enables a user to readily detect the change in color that occurs upon reaction of the diazonium ion with a nucleophilic aromatic compound. The diazonium ion may form an ionic and/or covalent bond with functional groups present on the surface of the chromatographic medium 23 so that it remains immobilized thereon. For instance, particles, such as described herein, may facilitate the immobilization of the diazonium ion at the detection zone 31. Namely, the diazonium ion may be coated onto particles, which are then immobilized on the chromatographic medium 23 of the device 20. In this manner, the diazonium ion is able to readily contact nucleophilic aromatic compounds flowing through the medium 23.

In one embodiment, the lateral flow device may include a plurality of substrates, each of which may be susceptible to cleavage by a different protease. According to this embodiment, the lateral flow device may be designed to examine a single test sample for more than one protease so as to identify a pathogen in the test sample with more particularity. For example, referring to FIG. 2, the lateral flow device 30 employs a first substrate susceptible to cleavage by a first protease, e.g., an aminopeptidase. The lateral flow device also includes a first detection zone 31, as described above, and within which is immobilized a first reagent that may interact with the cleaved chromogenic product released by the aminopeptidase.

Figure 2:
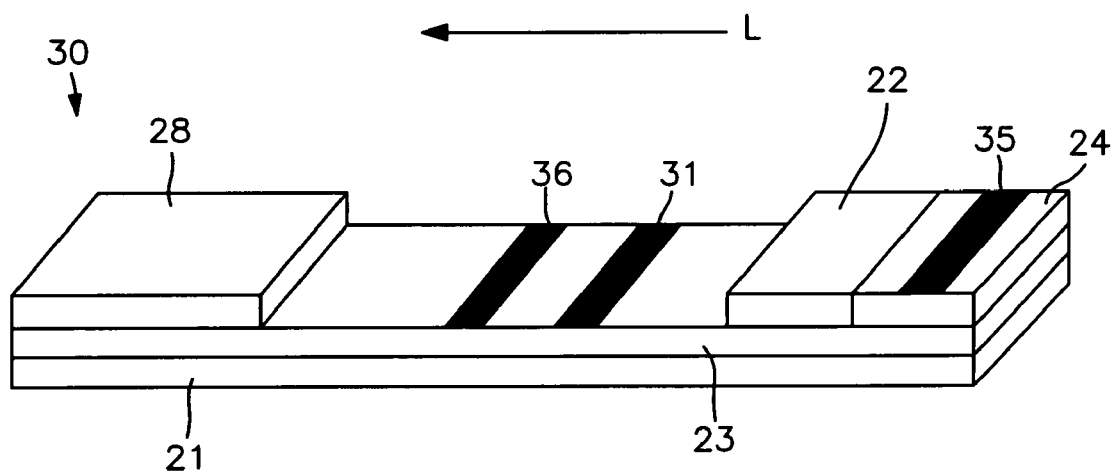
FIG. 2 is a perspective view of another embodiment of a lateral flow device that may be used in the present invention.

In addition, the lateral flow device of FIG. 2 may employ a second substrate susceptible to cleavage by a second protease, e.g., a second aminopeptidase, an aminoproteinase, etc. The second substrate may be mixed with the test sample prior to application to the device or the second substrate may be diffusively immobilized on the device either upstream or downstream of the first detection zone 31 prior to application of the test sample. The lateral flow device may also include a second detection zone 36. Within the second detection zone 36 may be immobilized a second reagent that may interact with the chromogenic product released by the second protease of interest. Moreover, the first and second reagents may be selected to be particular to the first and second chromogenic cleavage products, respectively, so as to prevent any cross reaction. In other words, the first reagent, immobilized in detection zone 31 will not interact with the second chromogenic product to produce a detectable color change, and the second reagent, immobilized in detection zone 36, will not interact with the first chromogenic product to produce a detectable color change in detection zone 31. For example, the first detection system may be an aromatic azo system and the second detection system may be an amino acid oxidase detection system. Accordingly, a positive result at first detection zone 31 may indicate the presence in the test sample of the first protease, and a positive result at second detection zone 36 may indicate the presence of the second protease. The combination of results may be utilized to identify the pathogen in the test sample with more particularity.

One benefit of the lateral flow device of the present invention is the ability to readily incorporate one or more additional reagent zones to facilitate the above-described protease-catalyzed reaction. For example, referring again to FIG. 1, one such zone is a quenching zone 35. The quenching zone 35 is configured to remove compounds from the test sample that would otherwise interfere with the accuracy of the detection system. For example, contaminants within the test sample (e.g., phenolics, bilirubin, urobilinogen, etc.) may react with the diazonium ion within the detection zone 31 and form an aromatic azo compound, thereby producing a "false negative" result. Thus, the quenching zone 35 may contain a quenching agent, such as a diazonium ion, that is capable of reacting with the reaction contaminants. The quenching agent may be the same or different than the detection agent used within the detection zone 31. Typically, the quenching agent is non-diffusively immobilized within the quenching zone 35 in the manner described above so that it does not flow through the medium 23 and interfere with testing. The location of the quenching zone 35 may vary, but is typically positioned upstream from the detection zone 31 and the location at which the substrate is applied to avoid interference with protease detection. For example, in the illustrated embodiment, the quenching zone 35 is positioned between the sample application zone 24 and the reagent zone 22. Alternatively, the quenching zone 35 may be positioned upstream from the sample application zone 24.

Another zone that may be employed in the lateral flow device 20 for improving detection accuracy is a control zone 32. The control zone 32 gives a signal to the user that the test is performing properly. More specifically, control reagents may be employed that flow through the chromatographic medium 23 upon contact with a sufficient volume of the test sample. These control reagents may then be observed, either visually or with an instrument, within the control zone 32. The control reagents generally contain a detectable substance, such as luminescent compounds (e.g., fluorescent, phosphorescent, etc.); radioactive compounds; visual compounds (e.g., colored dye or metallic substance, such as gold); liposomes or other vesicles containing signal-producing substances; enzymes and/or substrates, and so forth. Other suitable detectable substances may be described in U.S. Pat. Nos. 5,670,381 to Jou, et al. and 5,252,459 to Tarcha, et al., which are incorporated herein in their entirety by reference thereto for all purposes. If desired, the detectable substances may be disposed on particles (sometimes referred to as "beads" or "microbeads"), such as described above. Among other things, the particles enhance the ability of the detectable substance to travel through a chromatographic medium. Commercially available examples of suitable particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc. In addition, commercially available examples of suitable colored, latex microparticles include carboxylated latex beads sold by Bang's Laboratory, Inc.

The location of the control zone 32 may vary based on the nature of the test being performed. In the illustrated embodiment, for example, the control zone 32 is defined by the chromatographic medium 23 and positioned downstream from the detection zone 31. In such embodiments, the control zone 32 may contain a material that is non-diffusively immobilized in the manner described above and forms a chemical and/or physical bond with the control reagents. When the control reagents contain latex particles, for instance, the control zone 32 may include a polyelectrolyte that binds to the particles. Various polyelectrolytic binding systems are described, for instance, in U.S. Patent App. Publication No. 2003/0124739 to Song, et al., which is incorporated herein in it entirety by reference thereto for all purposes. In alternative embodiments, however, the control zone 32 may simply be defined by a region of the absorbent material 28 to which the control reagents flow after traversing through the chromatographic medium 23.

Regardless of the particular control technique selected, the application of a sufficient volume of the test sample to the device 20 will cause a detectable signal to form within the control zone 32, whether or not the protease is present. Among the benefits provided by such a control zone is that the user is informed that a sufficient volume of test sample has been added without requiring careful measurement or calculation. This provides the ability to use the lateral flow device 20 without the need for externally controlling the reaction time, test sample volume, etc.

In addition to the zones specified above, the lateral flow device 20 may also include other optional zones. For example, in one embodiment, the lateral flow device 20 may include an accelerator zone (not shown) in which is contained an accelerator for the protease-catalyzed substrate reaction. Typically, the accelerator is diffusively immobilized within the accelerator zone in the manner described above so that it may flow through the medium 23 upon contact with the test sample. The location of the accelerator zone may generally vary, so long as it positioned upstream from the detection zone 31. For example, in some embodiments, the accelerator zone may be positioned at a location (e.g., sample application zone 24) that is upstream from the application of the substrate (e.g., reagent zone 24). Due to the separation provided between the substrate and accelerator, the likelihood of any premature reaction therebetween is thus reduced. It should be understood, however, that the accelerator may nevertheless be combined with the substrate in some applications.

The detection zone 31, quenching zone 35, control zone 32, accelerator zone, and any other zone employed in the lateral flow device 20 may generally provide any number of distinct detection regions so that a user may better determine the concentration of the protease within the test sample. Each region may contain the same or different materials. For example, the zones may include two or more distinct regions (e.g., lines, dots, etc.). The regions may be disposed in the form of lines in a direction that is substantially perpendicular to the flow of the test sample through the device 20. Likewise, in some embodiments, the regions may be disposed in the form of lines in a direction that is substantially parallel to the flow of the test sample through the device 20.

One particular embodiment of a method for detecting the presence of a protease within a test sample using the device 20 of FIG. 1 will now be described in more detail. Initially, a test sample containing an aminopeptidase is applied to the sample application zone 24 and travels in the direction "L" to the reagent zone 22. At the reagent zone 22, the aminopeptidase is able to mix with and begin to initiate the catalytic reaction. As the mixture flows through the device 20, the aminopeptidase hydrolyzes the peptide bonds of the substrate and releases chromogenic products, such as nucleophilic aromatic compounds. The aromatic compounds then flow to the detection zone 31 where they react with a diazonium ion to form a colored azo compound. After the reaction, the detection zone 31 changes color. Thus, the color or color intensity of the detection zone 31 may be determined, either visually or with instrumentation. If desired, the intensity of the color at the detection zone 31 may be measured to quantitatively or semi-quantitatively determine the level of the aminopeptidase present in the test sample. The intensity of the color at the detection zone 31 is typically directly proportional to protease concentration. The intensity of the detection signal "$I_s$" produced at the detection zone 31 may also be compared to a predetermined detection curve developed for a plurality of known protease concentrations. To determine the quantity of protease in an unknown test sample, the signal may simply be converted to protease concentration according to the detection curve. Regardless, the protease, e.g., the aminopeptidase, and any unreacted substrate and/or aromatic compounds then travel past the detection zone 31 until they reach the absorbent material 28. In some cases, the aromatic compounds will oxidize over a period of time in air to form colored compounds. However, because such colored compounds are not located at the detection region 31, they generally do not interfere with the detection accuracy.

The present invention provides a relatively simple, compact and cost-efficient device for accurately detecting the presence of protease within a test sample (e.g., vaginal fluid). The test result may be visible so that it is readily observed by the person performing the test in a prompt manner and under test conditions conducive to highly reliable and consistent test results. The test is also less time-dependent. Accordingly, the present invention may provide a convenient, accurate determination of the presence of a pathogenic agent in the source of the test sample.

The present invention may be better understood with reference to the following example.

EXAMPLE

The ability to detect aminopeptidase in accordance with the present invention was demonstrated. Initially, an HF12002 nitrocellulose membrane laminated to a support card (Millipore, Inc.) was provided as the chromatographic medium. To form a detection zone, Diazo Red DC (DR) was initially striped by hand onto the membrane. The Diazo Red DC was in the form of a solution containing water and approximately 10 wt. % dimethylformamide ("DMF"). The membrane was then dried at 37° C. for two hours.

A cellulose pad was laminated to the one end of the membrane card to provide an absorbent or wicking pad.

A reagent pad was fabricated from a glass fiber pad having a length of 15 centimeters (Millipore Inc.). More specifically, the pad was soaked with 15 milliliters of a mixture containing (i) 1 wt. % Tween 20 (available from Sigma-Aldrich Chemical Co.) in 20 millimolar Tris buffer (pH=7.4); (ii) 0.5 milliliters of a solution containing 20 wt. % sucrose; and (iii) 0.2 milliliters of L-leucine β-naphthylamide (0.1 molar in DMF). The glass fiber pad was then dried at 37° C. for two hours and laminated to the other end of the membrane card. A cellulose sample application pad was then laminated to the glass fiber pad to provide a sample application zone. The fully assembled card was cut into 4-millimeter wide strip devices.

To test the device, a control sample (in Tris buffer, pH=7.4, 20 millimolar) and a positive aminopeptidase sample (100 micrograms per milliliter, in Tris buffer, pH=7.4, 20 millimolar) were prepared. The aminopeptidase was derived from *Streptomyces griseus* and obtained from Sigma. 150 microliters of each sample were then applied to the sample application zone of two separate devices. After approximately 15 minutes, each sample was visually observed. For the control sample, the detection zone remained yellow; however, for the positive aminopeptidase sample, the detection zone was red.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for detecting the presence of a protease within a test sample, the method comprising:
    i) providing a lateral flow assay device that comprises a fluidic medium, the lateral flow assay device comprising a sample application zone, the fluidic medium defining a detection zone within which is immobilized a first reagent, the detection zone being in fluid communication with a substrate, wherein the substrate is capable of cleavage by the protease and a chromogenic product is released upon the cleavage of the substrate by the protease;
    ii) contacting the sample application zone with the test sample, wherein the test sample travels through the fluidic medium from the sample application zone to the detection zone following contacting of the sample application zone with the test sample; and
    iii) generating a color within the detection zone that corresponds to the presence or absence of the protease in the test sample.

2. The method of claim 1, further comprising obtaining the test sample from a host, wherein the generated color indicates the presence of a pathogen in the host, wherein the pathogen expresses the protease.

3. The method of claim 2, wherein the pathogen is a yeast, bacteria, or parasite.

4. The method of claim 2, wherein the pathogen is pathogenic *Candida albicans*.

5. The method of claim 2, wherein the test sample is obtained from saliva.

6. The method of claim 2, wherein the test sample is obtained from vaginal fluid.

7. The method of claim 1, further comprising measuring the intensity of the generated color, wherein the amount of the protease in the test sample is proportional to the intensity of the generated color.

8. The method of claim 1, wherein the protease is a peptidase.

9. The method of claim 8, wherein the peptidase is an aminopeptidase.

10. The method of claim 8, wherein the peptidase is proline iminopeptidase.

11. The method of claim 1, wherein the fluidic medium further defines a second detection zone, the second detection zone being in fluid communication with a second substrate, wherein the second substrate is capable of cleavage by a second protease and a second chromogenic product is released upon the cleavage of the second substrate by the second protease, the method further comprising generating a second color within the second detection zone that corresponds to the presence or absence of the second protease in the test sample.

12. The method of claim 1, wherein the expression of the protease is upregulated by a hyphal form of *Candida albicans*.

* * * * *

UNITED STATES PATENT AND TRADEMARK OFFICE
CERTIFICATE OF CORRECTION

PATENT NO. : 7,575,887 B2  Page 1 of 1
APPLICATION NO. : 11/364810
DATED : August 18, 2009
INVENTOR(S) : Xuedong Song It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 468 days.

Signed and Sealed this

Seventh Day of September, 2010

David J. Kappos
*Director of the United States Patent and Trademark Office*